United States Patent [19]

Kirschner et al.

[11] Patent Number: 4,869,908
[45] Date of Patent: Sep. 26, 1989

[54] FIBER FORMULATIONS

[75] Inventors: Mitchell I. Kirschner, St. Louis; William H. Dorow, St. Charles, both of Mo.

[73] Assignee: K.V. Pharmaceutical Co., St. Louis, Mo.

[21] Appl. No.: 1,969

[22] Filed: Jan. 9, 1987

[51] Int. Cl.⁴ .................. A61K 9/02; A61L 15/03
[52] U.S. Cl. .................. 424/468; 424/469; 424/472; 424/473; 424/483; 424/486; 424/83; 424/195.1; 514/964
[58] Field of Search .......... 424/195.1, 83, 439, 424/468, 441, 469, 473, 472; 514/964, 483, 486

[56] References Cited

U.S. PATENT DOCUMENTS

| | | | |
|---|---|---|---|
| 3,965,256 | 6/1976 | Leslie | 424/468 |
| 4,292,299 | 9/1981 | Suzuki et al. | 424/472 |
| 4,369,172 | 1/1983 | Schor et al. | 424/468 |
| 4,565,702 | 1/1986 | Morley et al. | 426/93 |

FOREIGN PATENT DOCUMENTS 1405088  9/1975  United Kingdom ............... 424/468

Primary Examiner—John W. Rollins
Attorney, Agent, or Firm—Sandler & Greenblum

[57] ABSTRACT

Tablets containing nutritional and therapeutic substances in conjunction with dietary fiber substances. The tablets can be formulated in two layers which separate the nutritional and therapeutic substances from the fiber.

45 Claims, No Drawings

FIBER FORMULATIONS

BACKGROUND OF THE INVENTION

I. Field of the Invention

The present invention is directed to nutritional or therapeutic compositions. Specifically, the invention is concerned with nutritional or therapeutic compositions being administered in conjunction with dietary fiber substances.

II. Description of the Prior Art

Fibre substances have been used for nutritional purposes for many years. They are commonly found in breads and cereals. Fiber substances have also been provided in a variety of forms (tablets, powder, etc.) as a dietary supplement.

A significant problem in the oral delivery of nutritional and therapeutically active agents is the stomach retention time of many active agent for a sufficient period to effect the absorption of the active agent into the body. The stomach retention period is important to obtain the maximum level of absorption of the active agent. If the active agent passes through the stomach too quickly then less and possibly insufficient absorption is obtained and the delivery of the drug is less effective.

It is an object of this invention to provide a means for extending the stomach retention time of nutritionally or therapeutically active agents. A further object is to maximize the bioavailability of nutritionally or therapeutically active agents. Another object is to deliver the active agent in a form which maximizes the bioavailability of the active agent. A final object is to provide a means for separating the fiber component and the active agent component.

SUMMARY OF THE INVENTION

The invention is directed to a composition containing an agent which is to be absorbed primarily in the upper gastrointestinal tract which comprises a fiber substance and an active agent. The invention is further directed to a composition containing an active agent which is to be absorbed primarily in the upper gastrointestinal tract which comprises a tablet with at least two layers in which one layer is a fiber substance and the other layer contains an active agent.

DESCRIPTION OF THE PREFERRED EMBODIMENTS

Unique therapeutic combinations of fibre and drug or nutritional substances improves the absorption of the drug or nutritional substances in the body, thus, improving the bioavailability and efficiency of the product. This is due to the swelling action of the fiber, which thereby increases the retention of the product in the stomach. Therefore, the products of the invention attain maximum bioavailability through increased stomach retention which allows for maximum levels of absorption of the active agent(s). Those compositions that are water soluble and have active sites of absorption in the upper gastrointestinal tract are especially effective for use in the invention.

One embodiment involves tableting the compositions of the invention. Preferably, the tablet contains at least two layers. One layer contains the fibre and the second layer contains the active agent. By separating the substances the fiber does not bind up the active agents within the swelled fibre as it passes into the stomach.

It is important that the active agent be freely available for absorption in the stomach. Thus, binding or entrapment of the active agent by the fiber should be avoided. The active agent must be available for absorption thru the stomach walls. Preferably certain active agents exhibit their greatest bioavailability in a low pH environment. For these agents it is desirable that they be retained in the stomach as long as possible in order to achieve maximum absorption.

The following substances are suitable for use with the invention:

Fibre: Any natural or synthetic source of fiber, preferably those which are water soluble—non-limiting examples:

Natural Sources: Grains, such as oats, oat bran, and barley, and citrus fruits.

Synthetic Sources: Plastics, acrylates, such as polycarbophil and the salts thereof and cellulose complexes.

Therapeutic & Nutritional Composition (A) Therapeutic Product—non-limiting examples: appetite suppressants, analgesics, muscle relaxants, anti-diarrheals, laxatives, anti-hypertensives, hypoglycemics, oral diabetics, diuretics, tranquilizers, neurolytic, psychotropic compounds, antacids and antiulcers.

(B) Nutritional Products—non-limiting examples: All water-soluble vitamins (vitamins C, B complexes etc.), and minerals, including all sources of calcium magnesium, manganese, protein and protein derivatives, emulsifiers and lipophilics.

The following examples illustrate the formulation and manufacture of the products of the invention.

Description

A two-layer tablet that contains 600 mg. of fiber and 385 mg. commercially available Multivitamin/Multimineral (which is equivalent to one-fifth of the recommended daily allowance)

| Formula | Item # | Material | Amt./Tab | Percent |
| --- | --- | --- | --- | --- |
| 600 mg. | (1) | Natural Fiber - 44/60 Granulation | 600 mg./tab | 60.9% |
| 112 mg. | (2) | Microcrystalline Cellulose | | 11.4% |
| 77.6 mg. | (3) | Calcium from DiCalcium Phos. | | 7.9% |
| 60.4 mg. | (4) | Phosphate from Dicalcium Phos. | | 6.1% |
| 33.2 mg. | (5) | Magnesium from Magnesium Oxide | | 3.4% |
| 8.65 mg. | (6) | Zinc from Zinc Sulfate | | 2.2% |
| 19.5 mg. | (7) | Vit. C from Ascorbic Acid | | 1.98% |
| 16.4 mg. | (8) | Iron from Ferrous Fumerate | | 1.7% |
| — | (9) | Crospovidone XL | | 1.6% |
| 6.0 mg. | (10) | Potassium from Potassium Chloride | | 1.6% |
| 5.4 mg. | (11) | Chloride from Potassium Chloride | | 1.4% |
| 13.2 mg. | (12) | Vit. E from Vit. E Acetate | | 1.3% |
| 5.0 mg. | (13) | Selenium from Selenium Yeast | | 1.3% |

-continued

| Formula | Item # | Material | Amt./Tab | Percent |
|---|---|---|---|---|
| 4.4 mg. | (14) | Niacinamide | | 1.1% |
| 3.4 mg. | (15) | Manganese from Manganese Sulfate | | 0.9% |
| 2.5 mg. | (16) | Vit. A from Vit. A Acetate | | 0.6% |
| 2.4 mg. | (17) | Pantothenic Acid from d-Calcium Pantothenate | | 0.6% |
| — | (18) | Stearic Acid | | 0.5% |
| 2.0 mg. | (19) | Vit. $B_{12}$ From Cyanocobalamin | | 0.5% |
| — | (20) | Magnesium Stearate | | 0.3% |
| 0.94 mg. | (21) | Biotin | | 0.24% |
| 0.8 mg. | (22) | Pyridoxine from Pyridoxine Hydrochoride | | 0.21% |
| 0.6 mg. | (23) | Riboflavin | | 0.2% |
| 0.5 mg. | (24) | Copper from Cupric Oxide | | 0.14% |
| 0.48 mg. | (25) | Thiamine from Thiamine Mononitrate | | 0.12% |
| — | (26) | Syloid | | 0.09% |
| 0.2 mg. | (27) | Vit. D from Vit. $D_3$ | | 0.04% |
| 0.1 mg. | (28) | Folic Acid | | 0.03% |
| 0.05 mg. | (29) | Iodide from Potassium Iodide | | 0.01% |
| 0.03 mg. | (30) | Chromium from Chromium Chloride | | 0.00% |
| 0.013 mg. | (31) | Molybdenum from Sodium Molybdate | | 0.00% |
| | | Weight of Layer #2 | 385 mg/tab | |
| | | Total Tablet Weight | 985 mg/tab | |

Manufacturing Procedures

Layer #1 Direct Compression Material
Layer #2
Step 1 Premix item #s 22,23,25,26, and 28. Screen through a #35 mesh screen.
Step 2 Transfer to suitable blender along with approximately one half of item #4. Blend.
Step 3 Screen item #s 5, 6, 14, 15, 17, and 24 through a #35 mesh screen. Transfer to blender and blend.
Step 4 Transfer item #s 7, 8, 11, 12, 16, 19, to blender and blend.
Step 5 Premix item #s 2, 21, and 29. Screen through a #35 mesh screen. Blend with Step 4.
Step 6 Transfer item #s 10, 11, 13, and 27 to blender and blend.
Step 7 Grind item #s 30 and 31 with 300 mg. item #4. Transfer to blender in Step 6 and blend.
Step 8 Add the remainder of item #s 3 and 4. Blend.
Step 9 Add item #9. Blend
Step 10 Screen and add item #s 18 and 20. Blend.

Final Product

Step 1 Compress layer #1 and #2.
Step 2 Film coat clear.
Step 3 Package.

EXAMPLE II

Fiber 600 mg. Calcium 300 mg. Vitamin $D_3$ 31 IU

Description

A one-layer tablet that contains 600 mg. Fiber, 300 mg. Calcium and 31 IU Vitamin $D_3$

| | | Formula: | | |
|---|---|---|---|---|
| 44% Fiber | (1) | Natural Fiber 44/600 granulation | 600 | mg/tab |
| 300 mg. | (2) | Calcium Carbonate 92.8% D.C. (37% Ca) | 811 | mg/tab |
| 31 IU + 60% | (3) | Vitamin $D_3$ 100,000 IU/gm | 0.5 | mg/tab |
| — | (4) | Croscarmellose, sodium | 6.0 | mg/tab |
| — | (5) | Magnesium Stearate | 3.0 | mg/tab |
| | | Total Tablet Wt: | 1529 | mg/tab |

Manufacturing Procedure

Step 1 Transfer the natural fiber 44/600 gram (44% non-nutritive diet any fibre/600 mg of fibre granulation) to a suitable blender and hold for step 4.
Step 2 Premix Vitamin $D_3$ (having 60% overage of vitamin $D_3$) with equal amount of croscarmellose, sodium in a blender. Blend for (1) minute.
Step 3 Blend the material from Step 2 with the remaining portion of croscarmellose, sodium. Blend for (1) minute in the blender.
Step 4 Transfer the Premix (Vitamin $D_3$ and croscarmellose, sodium) to the blender in Step 1. Blend for 10 minutes.
Step 5 Screen the Magnesium Stearate through a #20 mesh screen and transfer to the blender in Step 4. Blend for 3 minutes.
Step 6 Compress the granulation on a suitable Rotary Press with 0.342"×0.746 mod. oval tooling at a target weight of 1420.5 mg/tab
Step 7 Film coat using a clear solution.

As previously noted that composition of the invention exhibit a number of unique properties. One of these properties is that it allows for the controlled release of the active agent. Due to the prolonged retention of the active agent in the stomach, the effects of a controlled release system are obtained.

I claim:
1. A composition containing an agent which is to be absorbed primarily in the upper gastrointestinal tract comprising: an active agent and a fibre substance which does not bind the active agent.
2. The composition according to claim 1 wherein said active agent contains at least one therapeutic agent.
3. The composition according to claim 1 wherein said active agent contains at least one nutritional substance.
4. The composition according to claim 1 wherein said fibre substance comprises natural fiber.
5. The composition according to claim 1 wherein said fibre substance comprises synthetic fibre.
6. The composition according to claim 2 wherein said fibre substance comprises a natural fiber.

7. The composition according to claim 3 wherein said fibre substance comprises a natural fiber.

8. The composition according to claim 2 wherein said fibre substance comprises a synthetic fiber.

9. The composition according to claim 3 wherein said fibre substance comprises a synthetic fiber.

10. The composition according to claim 7 wherein said nutritional substance comprises at least one vitamin.

11. The composition according to claim 9 wherein said nutritional substance comprises at least one vitamin.

12. The composition according to claim 7 wherein said nutritional substance comprises at least one mineral.

13. The composition according to claim 10 wherein said nutritional substance further comprises in addition to said vitamin at least one mineral.

14. The composition according to claim 9 wherein said nutritional substance comprises at least one mineral.

15. The composition according to claim 11 wherein said nutritional substance further comprises in addition to said vitamin at least one mineral.

16. The composition according to claim 12 wherein said mineral comprises calcium.

17. The composition according to claim 13 wherein said mineral comprises calcium.

18. The composition according to claim 14 wherein said mineral comprises calcium.

19. The composition according to claim 15 wherein said mineral comprises calcium.

20. A composition containing an active agent which is to be absorbed primarily in the upper gastrointestinal tract comprising a tablet with at least two layers wherein one layer contains an active agent and the other layer is a fibre substance that does not bind the active agent.

21. The composition according to claim 20 wherein said active agent contains at least one nutritional substance.

22. The composition according to claim 20 wherein said fibre substance comprises natuarl fibre.

23. The composition according to claim 20 wherein said fibre substance comprises synthetic fibre.

24. The composition according to claim 21 wherein said fibre substance comprises a natural fibre.

25. The composition according to claim 21 wherein said fibre substance comprises a synthetic fiber.

26. The composition according to claim 24 wherein said nutritional substance comprises at least vitamin.

27. The composition according to claim 25 wherein said nutritional substance comprises at least one vitamin.

28. The composition according to claim 24 wherein said nutritional substance comprises at least one mineral.

29. The composition according to claim 26 wherein said nutritional substance further comprises in addition to said vitamin at least one mineral.

30. The composition according to claim 25 wherein said nutritional substance comprises at least one mineral.

31. The composition according to claim 27 wherein said nutritional substance further comprises in addition to said vitamin at least one mineral.

32. The composition according to claim 28 wherein said mineral comprises calcium.

33. The composition according to claim 29 wherein said mineral comprises calcium.

34. The composition according to claim 30 wherein said mineral comprises calcium.

35. The composition according to claim 31 wherein said mineral comprises calcium.

36. The composition according to claim 20 wherein said active agent layer comprises at least two active agents.

37. The composition according to claim 20 wherein said active agent is an antacid.

38. The composition according to claim 20 wherein said active agent is an antiulcer drug.

39. The composition according to claim 20 wherein said active agent is a therapeutic drug.

40. The composition according to claim 20 wherein said fibre substance is water soluble.

41. The composition according to claim 20 wherein the retention of the active agent in the stomach is increased.

42. The composition according to claim 20 wherein the bioavailability of the active agent is increased.

43. The composition according to claim 20 wherein the absorption of the active agent is increased.

44. The composition according to claim 20 wherein the effects of a controlled release system of the active agent is obtained.

45. The composition according to claim 20 wherein said layer containing the fibre substance further comprises an active agent.

* * * * *

UNITED STATES PATENT AND TRADEMARK OFFICE
CERTIFICATE OF CORRECTION

PATENT NO. : 4,869,908

DATED : September 26, 1989

INVENTOR(S) : Mitchell I. KIRSCHNER et al.

It is certified that error appears in the above-identified patent and that said Letters Patent is hereby corrected as shown below:

Title page, item [57],
    in the Abstract, line 2, change "dietrary" to ---dietary---;
    Column 2, line 39, change "transquilizers" to ---tranquilizers---.
    Column 3, line 41, after "blend" insert ---.---.
    Column 5, line 44, change "natuarl" to ---natural---.
    Column 5, line 44, after "comprises" insert ---a---.
    Column 5, line 46, after "comprises" insert ---a---; and
    Column 6, line 2, after "least" insert ---one---.

Signed and Sealed this

Twenty-third Day of July, 1991

Attest:

HARRY F. MANBECK, JR.

Attesting Officer    Commissioner of Patents and Trademarks